US00PP35432P2

(12) United States Plant Patent
Lim

(10) Patent No.: US PP35,432 P2
(45) Date of Patent: Oct. 24, 2023

(54) ROSE PLANT NAMED 'ALTSANTARED'

(50) Latin Name: *Rosa hybrida*
Varietal Denomination: ALTsantared

(71) Applicant: Altman Specialty Plants Inc., Vista, CA (US)

(72) Inventor: Peter Lim, Escondido, CA (US)

(73) Assignee: Altman Specialty Plants Inc, Vista, CA (US)

( * ) Notice: Subject to any disclaimer, the term of this patent is extended or adjusted under 35 U.S.C. 154(b) by 0 days.

(21) Appl. No.: 18/091,749

(22) Filed: Dec. 30, 2022

(51) Int. Cl.
*A01H 5/02* (2018.01)
*A01H 6/74* (2018.01)

(52) U.S. Cl.
USPC ..... Plt./151
CPC ..... *A01H 6/749* (2018.05)

(58) Field of Classification Search
USPC ..... Plt./151
CPC ..... A01H 6/749; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Rosa* plant named 'ALTsantared' is disclosed, characterized by distinctive fully double dark red flowers with a tea rose fragrance. Plants are vigorous and can be grown on their own roots. Plants bloom early, flower continuously, and exhibit good resistance to blacks pot (*Diplocarpon rosae*) and powdery mildew (*Podosphaera pannosa*) diseases. The new variety is a *Rosa*, normally produced as an outdoor garden or container plant.

1 Drawing Sheet

Latin name of the genus and species: *Rosa hybrida.*
Variety denomination: 'ALTsantared'.

BACKGROUND OF THE INVENTION

The new *Rosa* cultivar is a product of a planned breeding program conducted by the inventor, Peter Ping Lim. The objective of the breeding program was to produce vigorous new garden rose varieties with continuous blooming for ornamental commercial applications. The cross resulting in this new variety was made during June of 2013 in Vista, Calif.

The seed parent is the variety *Rosa* 'WEKBIJOU', U.S. Plant Pat. No. 23,269. The pollen parent is an unnamed, unpatented red flowered shrub rose seedling. The new variety was selected in June of 2014 by the inventor in a group of seedlings resulting from the 2013 crossing, in a nursery in Vista, Calif.

Asexual reproduction of the new cultivar has been performed by vegetative cuttings. This was first performed at a research greenhouse in Vista, Calif. in June 2014 and has shown that the unique features of this cultivar are stable and reproduced true to type in more than 5 successive generations.

SUMMARY OF THE INVENTION

The cultivar 'ALTsantared' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ALTsantared' These characteristics in combination distinguish 'ALTsantared' as a new and distinct *Rosa* cultivar:

1. Double flowers composed of 60 to 70 petals.

2. Dark red flower color.
3. Early blooming.
4. Dark glossy foliage resistant to black spot and powdery mildew disease.
5. Plants can be grown on their own roots; grafting is not required.

PARENT COMPARISONS

Plants of the new cultivar 'ALTsantared' are similar to plants of the seed parent, in most horticultural characteristics, however, plants of the new cultivar 'ALTsantared' differ in the following:

1. Flowers of the new cultivar have a deeper red color than flowers of the seed parent.
2. Petal count of the new variety is higher than petal count of the seed parent.
3. Flower color of the new variety is dark red; flower color of the seed parent is lavender-bronze.

Plants of the new cultivar 'ALTsantared' are similar to plants of the pollen parent in most horticultural characteristics, however, plants of the new cultivar 'ALTsantared' differs in the following;

1. Plant size of the new variety is smaller than plant size of the pollen parent.

COMMERCIAL COMPARISONS

Plants of the new cultivar 'ALTsantared' can be compared to the commercial variety *Rosa* 'Legends', unpatented. These varieties are similar in most horticultural characteristics, however 'ALTsantared' differs in the following:

1. Flowers of the new variety produce more petals than this comparator.
2. Flowers of the new variety have a tea rose fragrance, while flowers of this comparator have no noticeable fragrance.

3. The new variety is a smaller plant than this comparator.
4. Flowers of the new variety are dark red, while flowers of this comparator are medium cherry red.

Plants of the new cultivar 'ALTsantared' can also be compared to the commercial variety *Rosa* 'Love's Magic', unpatented. These varieties are similar in most horticultural characteristics, however 'ALTsantared' differs in the following:

1. Flowers of the new variety have more petals than this comparator.
2. The new variety is a smaller plant than this comparator.

BRIEF DESCRIPTION OF THE PHOTOGRAPH

The accompanying photograph illustrates in full color a close up of an individual flower from a plant of about 18 months old. The photograph was taken using conventional techniques and although colors may appear different from actual colors due to light reflectance it is as accurate as possible by conventional photographic techniques

DETAILED BOTANICAL DESCRIPTION

In the following description, color references are made to The Royal Horticultural Society Colour Chart 2007 except where general terms of ordinary dictionary significance are used. The following observations and measurements describe 'ALTsantared' plants grown outdoors, in Palm Desert, Calif. The growing temperature ranged from approximately 10° C. to 38° C. during the day and from approximately 5° C. to 22° C. during the night. Measurements were taken in September. General light conditions were very bright, normal sunlight. Measurements and numerical values represent averages of typical plant types.

Botanical classification: *Rosa* 'ALTsantared'.

Market classification: Floribunda shrub rose.

PROPAGATION

Time to initiate roots: About 15 days at approximately 20° C.

Time to produce a rooted cutting: About 35 days at approximately 20° C.

PLANT

Age of plant described: Approximately 1.5 years.

Growth habit: Compact.

Container size: 2 gallon.

Height: 45 cm.

Plant spread: 55 cm.

Rootstock: Own root.

Growth rate: Moderate.

Branching characteristics: Sympodial branching.

Length of primary lateral branches: Average range 12 to 24 cm.

Diameter of lateral branches: Approximately 6 mm to 9 mm.

Quantity branches: 5 to 7 main branches, moderate lateral branches, 8 to 12 lateral branches per main branch.

Branches-young wood:

*Diameter*.—Approximately 4 mm.

*Texture*.—Glabrous, very dense soft, short thorns. As branch matures thorns become less dense and sharp.

*Color*.—Near RHS Green 143C.

Branches-old wood:

*Diameter*.—Approximately 5 to 8 mm.

*Color*.—Near RHS Green 137B.

*Texture*.—Glabrous.

Thorns:

*Approximately density/quantity of thorns*.—Young growth: Sparse, soft prickles. Occasional fully formed thorn colored near RHS Greyed-Red 181A about 3 to 4 mm long. Mature growth: Sparsely thorns about 3 mm at base, 3 mm long. Colored near RHS Grey-Orange N167C. Straight, not hooked.

FOLIAGE

Leaf:

*Arrangement*.—Alternate and compound.

*Quantity*.—Average 6 to 10 per main branch.

*Internode*.—Average range 3 cm to 5 cm.

*Average length*.—Approximately 9 to 12 cm.

*Average width*.—Approximately 7 cm.

Rachis:

*Average length*.—Approximately 4.0 cm to 5.0 cm.

*Average diameter*.—Approximately 2 mm.

*Color*.—Upper surface: Near RHS Green 137C. Lower surface: Near RHS Yellow-Green 144B.

*Texture*.—Glabrous, all surfaces.

Leaflet:

*Quantity*.—5 or 7 per leaf, most commonly 5.

*Average length*.—Approximately 3.5 cm to 4 cm.

*Average width*.—Approximately 3.0 cm to 3.8 cm.

*Shape of blade*.—Broad ovate.

*Apex*.—Acute.

*Base*.—Broadly rounded.

*Margin*.—Finely serrate. Serrations minute.

*Appearance of top surface*.—Strong glossy.

*Appearance of bottom surface*.—Matte.

*Texture of top surface*.—Glabrous.

*Texture of bottom surface*.—Glabrous.

*Color*.—Young foliage upper side: Near RHS Green 137B overall lightly flushed Greyed-Purple 187B. Margin 187A. Young foliage under side: Near RHS Green 137C overall lightly flushed Greyed-Purple 187B. Margin 187A. Mature foliage upper side: Near RHS Green 139A. Mature foliage under side: Near RHS Green 137A.

*Venation*.—Type: Reticulate. Venation color upper side: Near RHS Yellow-Green 144A, flushed Greyed-Purple 187B when immature. Venation color under side: Near RHS Green 143B.

Petiole:

*Average length*.—Approximately 1.8 cm to 2.5 cm.

*Average diameter*.—Approximately 3 mm.

*Color*.—Upper surface: Near RHS Yellow-Green 144C. Based flushed with anthocyanin near 187D. Lower surface: Near RHS Green 143C.

*Petiole wing*.—Typically 15 mm long and 5 mm wide. Apex apiculate. Upper surface colored near RHS Green 143A, lower surface colored near Green 137D.

*Texture*.—Glabrous.

FLOWER

Natural flowering season: Spring until Autumn.

Inflorescence type and habit: Singly occurring fully double rotate flowers.

Rate of flower opening: Approximately 7 days from bud to fully opened flower.

Flower longevity on plant: 10 to 14 days, after fully opened.
Quantity of flowers: About 10 to 15 fully opened flowers and buds.
Flower shape:
*From above*.—Round to very slightly irregular round.
*Profile of upper part of flower*.—Flattened convex.
*Profile of lower part of flower*.—Flattened convex.
Flower size:
*Diameter*.—Approximately 8 cm.
*Height*.—Approximately 5.8 cm.
Peduncle:
*Length*.—3.5 cm to 5.0 cm.
*Diameter*.—3 mm.
*Color*.—Near RHS Green 143C flushed Red 53A near flower attachment.
*Texture*.—Very softly prickly.
Petals:
*Petal arrangement*.—Multiple rotate, overlapping whorls.
*Petal quantity*.—Average 60 to 70.
*Length*.—3.5 cm.
*Width*.—3.5 cm.
*Shape*.—Orbicular.
*Margin*.—Entire. Curled downward.
*Apex*.—Rounded.
*Base*.—Very broad attenuate.
*Texture*.—Glabrous, all surfaces.
*Color*.—When opening: Upper surface: Near RHS Red 46A. Very small basal blotch near White N155C. Lower surface: Near RHS Red 53B. Very small basal blotch near White N155C. Fully opened: Upper surface: Near RHS Red 45A flushed 53A. Very small basal blotch near White N155C. Lower surface: Near RHS Red 53B. Very small basal blotch near White N155C.
Bud:
*Shape*.—Ovate.
*Length*.—Approximately 3.0 cm.
*Diameter*.—Approximately 2.2 cm.
*Color*.—Near RHS Red 46A.
Sepals:
*Quantity*.—5.
*Length*.—2.5 cm.
*Width*.—9 mm.
*Shape*.—Deltoid.
*Apex*.—Apiculate. No sepal extensions.
*Margin*.—Entire.
*Texture*.—Densely pubescent upper surface, slightly pubescent lower surface.
*Color*.—Interior Surface: Near RHS Green 138B flushed Red 53A. Exterior Surface: Near RHS Green 138A flushed Red 53A.
Receptacle:
*Length*.—14 mm.
*Width*.—16 mm.
*Shape*.—Flat.
*Color*.—Near RHS Yellow-Green 145D.
Fragrance: Moderate tea rose scent.

REPRODUCTIVE ORGANS

Stamens:
*Quantity*.—About 100.
*Filament length*.—Approximately 4 mm to 9 mm.
*Filament color*.—Near RHS Yellow-Orange 21B.
Anthers:
*Length*.—2 mm.
*Shape*.—Bi-lobed.
*Color*.—Near RHS Yellow-Orange 21A.
*Pollen*.—Color: Near RHS Yellow-Orange 18D. Quantity: Scant or none.
Pistil: Not observed.

OTHER CHARACTERISTICS

Seeds and fruits: Not observed.
Disease/pest resistance: Good overall resistance to normal pests typical of garden roses. Very good resistance to blackspot (*Diplocarpon rosae*). Very good resistance to powdery mildew (*Podosphaera pannosa*). In a three-year confidential field trial of floribunda shrub roses the new variety 'ALTsantared' remains free of powdery mildew year-round while varieties planted nearby showed symptoms of powdery mildew.

What is claimed is:

1. A new and distinct cultivar of *Rosa* plant named 'ALTsantared' as herein illustrated and described.

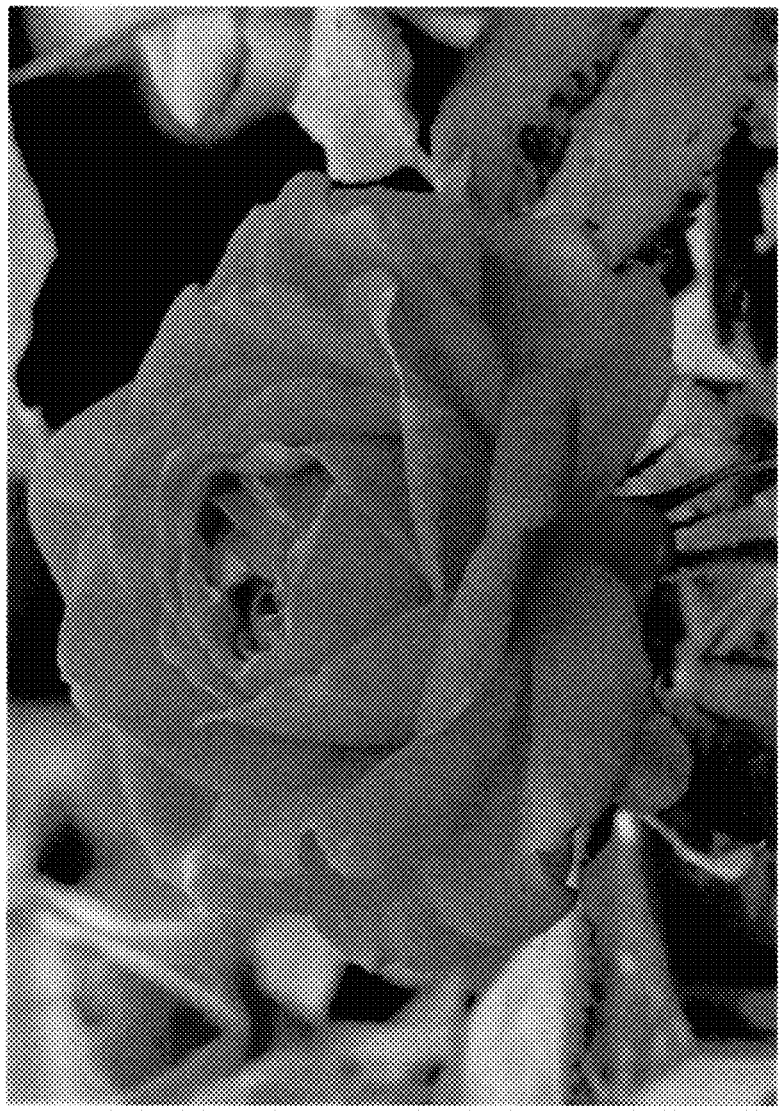

* * * * *